United States Patent [19]

Kamentsky

[11] Patent Number: 5,202,230
[45] Date of Patent: Apr. 13, 1993

[54] METHODS OF DETECTING CUT CELLS IN A TISSUE SECTION

[76] Inventor: Louis A. Kamentsky, 180 Beacon St., Apt. #17G, Boston, Mass. 02116

[21] Appl. No.: 912,028

[22] Filed: Jul. 9, 1992

Related U.S. Application Data

[63] Continuation of Ser. No. 579,049, Sep. 7, 1990, abandoned.

[51] Int. Cl.$^5$ .................. C12Q 1/68; C12N 13/00; G01N 33/48
[52] U.S. Cl. .................................... 435/6; 436/63; 436/64
[58] Field of Search ............... 435/6, 173; 436/63, 436/64

[56] References Cited

U.S. PATENT DOCUMENTS

| | | | |
|---|---|---|---|
| 3,918,812 | 11/1975 | Holm | 356/73 |
| 4,125,828 | 11/1978 | Resnick et al. | 340/146.3 |
| 4,284,412 | 8/1981 | Hansen et al. | 23/230 |
| 4,647,531 | 5/1987 | Kamentsky | 435/7 |
| 4,665,553 | 5/1987 | Gershman et al. | 382/6 |
| 4,741,043 | 4/1988 | Bacus | 382/6 |
| 4,880,752 | 8/1989 | Keck et al. | 435/7.72 |
| 4,889,690 | 12/1989 | Opitz et al. | 422/73 |

FOREIGN PATENT DOCUMENTS 2508523 7/1979 Fed. Rep. of Germany.

OTHER PUBLICATIONS

Brox et al. Dialog Abstract Embase No. 81159845 Cancer (Philadelphia) (USA) 1981, 47/10 (2433-2436).
Vanderlaan et al. Dialog Abstract Embase No. 83206973 Carcinogenesis (England) 1983, 4/6 (721-727).
Franklin et al. Dialog Abstract No. 04412687 J. Histochem Cytochem Apr. 1981 29(4) 572-576.
Hemstreet et al. Dialog Abstract Embase No. 83183177 Int. J. Cancer (Switzerland), 1983, 31/5 (577-585).
Bauer, Acta. Orthop. Scand. 59:5-39, 1989.
Stryer, Ann. Rev. Biochem. 47:819-46, 1978.
Koss et al., Human Pathology 20:528-548, 1989.

Megla, G. K., *The LARC Automatic White Blood Cell Analyzers*, Acta Cytologica, vol. 17(1):3-14(1973).
Green, J. E., *A Practical Application of Computer Pattern Recognition Research: The Abbott ADC-500 Differential Classifier*, J. Histochem. and Cytochem., vol. 27(1):160-173 (1979).
Shack, R. et al., *Ultrafast Laser Scanner Microscope*, J. Histochem. Cytochem., 27(1):153-159 (1979).
Reich, S., *Precision digital position encoding for resonant scanners*, SPIE Laser Scanning Recording, vol. 498:169-174 (1984).
Reich, S., *The Use of Electro-mechanical Mirror Scanning Devices*, SPIE Laser Scanning Components & Techniques, vol. 84:47-56 (1976).
Tweed, D. G., *Resonant Scanner Linearization Techniques*, SPIE Laser Scanning and Recording, vol. 498:161-168 (1984).
Martin, J. C., *Time: A New Parameter for Kinetic Measurements in Flow Cytometry*, Science vol. 207:199-201, (1980).
Bartels, P. H. et al., *Computer Analysis Biomedical Interpretation of Microscopic Images: Current Problems and Future Directions*, Proceedings of the IEEE, vol. 65 (2):252-261 (1977).
Carlsson, K., et al., *Confocal Imaging for 3-D Digital Microscopy*, Applied Optics, vol. 26(16):3232-3238 (1987).
Burger D., et al., *Acousto-Optic Laser-Scanning Cytometer*, Cytometry, vol. 9:101-110 (1988).

(List continued on next page.)

*Primary Examiner*—Margaret Moskowitz
*Assistant Examiner*—Kenneth R. Horlick
*Attorney, Agent, or Firm*—Fish & Richardson

[57] ABSTRACT

A method of identifying a sectioned cell in a tissue section including: supplying a tissue section; labeling cells of the tissue section with a detectable label; and selectively detecting the label from cells at the surface of the tissue section.

4 Claims, 2 Drawing Sheets

OTHER PUBLICATIONS

Kamentsky, L. A., *Cell Identification and Sorting*, Chapter 4, Computers in Biochemical Research, 3 (1969) (107–144).

Kamentsky, L. A., *Future Directions for Flow Cytometry*, J. Histochem. Cytochem., vol. 27(12): 1649–1651 (1979).

Shoemaker, R. L., et al. *An Ultrafast Laser Scanner Microscope for Digital Image Analysis*, IEEE Transactions on Biomedical Engineering, vol. BME–29 (2):82–91 (1982).

Van Driel–Kulker, A. M. J., et al., *The Use of LEYTAS in Analytical and Quantitative Cytology*, IEEE Transactions on Biomedical Engineering, vol. BME–29(2):92–100, (1982).

Mellors, R. C. et al., *Microfluorometric Scanner for the Differential Detection of Cells: Application to Exfoliative Cytology*, Science, vol. 114–356–360 (1951).

Sawyer, H. S. et al., *A New Nipkon–Disk Scanner for Accurate Cytological Measurements*, I.R.E. National Convention Record, Part 9:37–42 (1958).

McCarthy, B. D., *Automatic Determination of Morphological Parameters in Biological Materials by a Flying Spot Microscope*, Cytology Automation: Proceedings of Second Tenovus Symposium (1968) (231–242).

Lovett, E. J., et al., *Application of Flow Cytometry to Diagnostic Pathology*, Laboratory Investigation, vol. 50(2):115–139 (1984).

Cambridge Instruments, Quantimet 520, Image Analysis System (1986?).
Cell Analysis System, CAS 100 System (1985).
Perceptics Corporation, BioVision (1987).
Meridian Instruments, Inc. ACAS 470 (1986).
Tracor Northern, TSM.
Becton Dickinson, FACScan (1986).
Coulter Corporation, PROFILE.

METHODS OF DETECTING CUT CELLS IN A TISSUE SECTION

This is a continuation of application Ser. No. 07/579,049, filed Sep. 7, 1990, now abandoned.

BACKGROUND OF THE INVENTION

This invention relates to tissue sample analysis, and more particularly to the identification of sectioned or cut cells in tissue sections.

During the last thirty years there has been considerable interest in developing techniques for measuring the DNA content of biological cells. These techniques have been applied to the study of cells from tissue or from body fluids of cancer patients. It is generally believed that these tests can provide information useful for (1) diagnosing cancer, (2) determining the prognosis of a diagnosed cancer, and (3) treating the cancer.

DNA content is a useful diagnostic or prognostic parameter in part because of the fundamental principle that the DNA content of normal cells of any given species falls into a well characterized frequency distribution. The characteristic distribution of per cell DNA occurs because virtually all somatic cells, except when preparing for cell division, possess a specific quantity, (called $G_0$) of DNA in their nuclei. Prior to their division into two daughter cells, non-resting cells synthesize new DNA, increasing their DNA content to twice $G_0$. Cells having the double, or $G_2$, amount of DNA eventually undergo mitosis and cytokinesis, dividing into two daughter cells, each with the $G_0$ amount of DNA. Thus, if many body cells are each measured for their DNA content, and the number of cells for each DNA value measured is plotted against DNA value, a curve with peaks at the DNA values $G_0$ and $G_2$ is obtained. The curve also exhibits positive values for DNA content between these two peaks, the values between the peaks being dependent on the rate of synthesis of new DNA. In the ideal measurement system these two peaks are narrow, as there is little biological variation in the $G_0$ DNA value of any individual's normal cells.

It has been known for the last 50 years that cancer cells may have a resting DNA value different than $G_0$. The appearance of a population of cells with a DNA value that diverges from the normal is due to the occurrence of one or more abnormal mitotic events. Abnormal mitotic divisions give rise to clones of cells with DNA values above or below $G_0$. If such a cancer, i.e., a cancer with cells containing an abnormal amount of DNA, is present in a sample of body cells being measured, complex distributions of DNA, with more than the two peaks representing the $G_0$ and $G_2$ DNA values, are often found.

During the last 30 years aberrant DNA distributions in biological samples have been studied as a potential marker for the presence of cancer in the patient from whom the sample was taken. During the last 10 years there have been many hundreds of publications showing that there may be a relationship between the prognosis of a patient and consequently how that patient should be treated for his cancer and the distribution of DNA of his cancer cells. In general, it appears that the more aberrant the DNA distribution, the worse the chance of survival of a given patient for many cancers and the more aggressively that patient should be treated.

A number of approaches have attempted to apply these observations in clinically useful ways. A critical review of research in this area as well as an extensive bibliography can be found in L. G. Koss et al, Flow Cytometric Measurements of DNA and Other Cell Components in Human Tumors: A Critical Appraisal, Human Pathology 20, pp. 528-548, 1989, the disclosure of which is hereby incorporated by reference.

Two major approaches have been developed to measure cell constituents such as DNA. In the first, cells from either a body fluid, e.g., blood, or a body cavity are smeared on to a microscope slide and the slide stained such that the constituent of interest, e.g., DNA, of the cells will absorb light at any point on the slide in an amount proportional to the DNA at that point. The user, looking through a microscope scanning instrument, visually finds cells to be measured. For each such cell, the instrument images that illuminated cell using either a high resolution scanning light spot or camera. Light transmitted through the cell for each picture element is added and the sum of these, which is proportional to the DNA of the cell, is read out to the user or recorded in a data base. Since the dye used to measure the cell can be visually observed the user can find cells he believes to be intact cancer cells. The resulting DNA distribution of the sample can be prognostic of the patient's cancer. This procedure uses the human observer to find representative intact cells on isolated cell samples from body fluids or other samples consisting of isolated dispersed cells.

The method described above generally requires dispersed samples, as opposed to tissue sections or slices, in order to segment, i.e., distinguish, neighboring cells (as are found in tissue sections) from one another and to avoid confounding signals from cut or sectioned cells at the cut surfaces of tissue sections.

Several problems associated with the use of dispersed samples limit the value of approaches that use dispersed samples. Because the number of normal cells far exceeds the number of abnormal cells in most samples of either type, the abnormal DNA values, if present, can be obscured by the $G_0$ values of the normal cells in the tissue and thus not be found. This problem can be addressed in methods where the sample is a tissue section because the user can locate putative cancer cells from morphological characteristics of the tissue section and gather data on such a subset of cells. Thus the use of tissue sections as samples increases the chances of identifying a population of cells with an abnormal $G_0$ value. Because the information inherent in the morphology of the tissue is lost in dispersed or disrupted samples, this approach is not possible in techniques limited to these sample types. Furthermore, the procedures used to separate cells from one another in the preparation of a sample of dispersed cells (usually enzymatic digestion or mechanical disruption) generate large amounts of cell debris and damaged cells, both of which interfere with analysis.

The number of cells that must be measured in most applications requires the use of automated instruments. Attempts to automate the technique described above have been largely unsatisfactory. The specimens used with automated instruments, e.g., microscope slide scanners, are usually either body fluid cells or tissue that is minced and enzymatically treated to separate individual cells from one another. Thus these efforts generally suffer from the drawbacks discussed above regarding dispersed samples.

The second major approach referred to above has involved the use of flow cytometers. Flow cytometers, which have been commercially available since 1970, are used to measure DNA and other cell constituents in a broad variety of applications. These instruments measure multiple optical properties including fluorescence at different wavelengths and scatter at different angles, of cells flowing in a capillary past a light excitation whose source can be a laser or arc lamp. The cells analyzed are dispersed and stained to produce fluorescence proportional to one or more cellular constituents of interest. Flow cytometers operate automatically at measurement rates of 1000's of cells per second, provided that samples of isolated cells are available in liquid suspension.

Although flow cytometers measuring per cell DNA have been widely used for cancer prognosis, there is considerable criticism of the accuracy of the results. All of the problems associated with the measurement and interpretation of data gathered with non-flow instruments, e.g., microscope slide scanners, are present when flow cytometers are used. With a flow cytometer, which uses dispersed samples, it is impractical or impossible to obtain DNA distributions on only the cancer cells in a specimen, thus it is impossible or impractical to isolate data representative of just the cancerous part of the tissue specimen. As in the previously discussed techniques, the vast number of normal $G_0$ cells may obscure the measurement of other cell populations. Since the cells must flow through a capillary in single file, the sample must be traumatically treated to yield suspensions of single nuclei or cells. These samples are contaminated with debris and damaged cells that can interfere with subsequent data analysis.

SUMMARY OF THE INVENTION

In general, the invention features a method of identifying a sectioned cell in a tissue section including: supplying a tissue section; labeling cells of the tissue section with a detectable label; and selectively detecting the label, preferably with a multiple measurement fluorescence scanner, from cells at the surface of the tissue section Selectively detecting the label means detecting a unique signal from cells at the surface of the section, without substantial contribution from cells embedded in the section (embedded cells are cells that are not at the surface of the section), preferably by means of an automatic detection device. Preferred embodiments include those in which, the cells are labeled with a dye capable of being selectively detected only when positioned at the surface of the tissue section, e.g., where the dye is a partner in an energy transfer detection system, the energy transfer detection system preferably including the dye and an energy receiving/ transmitting component, or where a cut face of the tissue section is contacted with a substrate, e.g., to allow the dye to be irradiated with evanescent light passing the interface between the substrate and the tissue section. In other preferred embodiments, the label stoichiometrically labels a cell constituent, more preferably the stoichiometric label can be detected from cells that are not on the surface of the tissue section. In other preferred embodiments, detection of the label on embedded cells, i.e., cells that are not at the surface of the tissue section, and separately, the selective detection of label from cells at the surface of the section, are performed with a multiple measurement fluorescence scanner. Separately detecting means that the label, dye, or cells, detected at or in close proximity to the surface of the tissue section can be distinguished from label, dye, or cells, detected that are not at the surface of the tissue section.

The invention also features a method of identifying a sectioned cell in a tissue section which also includes: supplying a tissue section; supplying a dye, preferably an energy emitting dye; staining cells of the tissue section with the dye; irradiating the stained tissue section with light of a wavelength absorbed by the dye; and detecting, preferably with a multiple measurement fluorescence scanner, an optically detectable event, the occurrence of the optically detectable event being a function of, i.e., being dependent on, the proximity of a stained cell to a cut surface of the tissue section, the occurrence of the optical event identifying the stained cell as a sectioned cell. In preferred embodiments, the dye is a fluorescent dye; the dye binds only to the nucleus of the cells of the tissue section and the identified sectioned cell contains a sectioned nucleus; or the dye binds stoichiometrically to a cellular constituent. In other preferred embodiments the method includes staining the cells of the tissue sections with a second dye, preferably a fluorescent dye, the second dye being capable of stoichiometric binding to a cellular component. In yet other preferred embodiments, where the dye, or the second dye, binds stoichiometrically to a cell constituent, the presence of the dye, or the second dye, on cells not at the surface of the tissue section, i.e., on cells embedded in the tissue section, is detected. In yet other preferred embodiments, a multiple measurement fluorescence scanner is used to detect the optical event marking a sectioned cell and separately, to detect the presence of the dye, or second dye, on embedded cells, i.e., cells that are not at the surface of the tissue section.

The invention also features a method of identifying a sectioned cell in a tissue section including: supplying a tissue section; supplying an energy transferring dye pair, the dye pair including a first dye and a second dye, the emission spectrum of the first dye overlapping the absorption spectrum of the second dye, the overlap being sufficient to result in a detection enabling amount of energy transfer from the first dye to the second dye, the peak of the absorption spectrum of the first dye being sufficiently separated from the peak of the absorption spectrum of the second dye to allow a signal representing emissions from the second dye, the emissions from the second dye excited by absorbing emissions of the first dye (the emission of the first dye excited by energy of a wavelength absorbed by the first dye), to be distinguished from a signal representing emissions of the second dye excited directly by energy of the wavelength used to excite the first dye, and the peak of the emission spectrum of the first dye being sufficiently separated from the peak of emission of the second dye to allow a signal representing emissions from the second dye to be distinguished from a signal representing emissions from the first dye; staining the cells of the tissue section with the first dye; contacting a face of the stained tissue section with the second dye, the second dye preferably contained in or coated on a substrate; irradiating the stained tissue slice with energy in the absorption spectrum of the first dye; and detecting, preferably with a multiple measurement fluorescence scanner, a signal representing the emission of the second dye, the signal indicating the presence of a sectioned cell. In preferred embodiments, the first dye may be any of the following: a fluorescent dye, e.g., Hoechst 33258, Hoechst 33342 or 4',6-diamidine-2-phenylindole (DAPI). In preferred embodiments the first dye is stoichiometric for a cellular component, preferably a nuclear component, e.g., DNA. In preferred embodiments the second dye may be a fluorescent dye, e.g., ethidium bromide or propidium iodide. In other preferred embodiments, the method includes staining the tissue section with a third dye, the third dye being stoichiometric for a cell component, preferably a nuclear component, e.g., DNA. The third dye is chosen such that it does not interfere with the detection of the emission of the second dye, e.g., when the tissue section is irradiated with energy of the wave length used to excite the first dye a signal representing emissions of the second dye can be distinguished from a signal representing emissions from the third dye. In yet other preferred embodiments, where the second dye, or the third dye, is stoichiometric for a cell constituent, the presence of the second dye, or the third dye, on cells not at the surface of the tissue section is detected. In yet other preferred embodiments, a multiple measurement fluorescence scanner is used to detect the emission signaling the presence of a cut or sectioned cell and separately, to detect the presence of the second dye, or the third dye, on an embedded cell, i.e., on a cell that is not at the surface of the tissue section.

The invention also features a method of identifying a sectioned cell in a tissue section including: supplying a tissue section; supplying a first dye, preferably an energy emitting dye, more preferably a fluorescent dye, e.g., propidium iodide; staining the cells of the tissue section with the first dye; contacting the stained tissue section with a substrate; passing light through the substrate parallel to the plane of the tissue section; and detecting, preferably with a multiple measurement fluorescence scanner, the emission of light of the wavelength emitted by the first dye when the first dye is excited by evanescent light passing through the interface between the substrate and the tissue section, the emission of the light indicating close proximity of the cell to the substrate. In preferred embodiments, the first dye is stoichiometric for a cellular component, e.g., a nuclear component, e.g., DNA. In other preferred embodiments the method further includes staining the tissue slice with the second dye, the second dye being stoichiometric for a cell component, e.g., a nuclear component, e.g., DNA. The second dye is chosen such that it does not interfere with detection of the first dye, e.g., when the tissue section is irradiated with light of the wavelength used to excite the first dye a signal representing emissions of the first dye can be distinguished from a signal representing emissions of the second dye. In other preferred embodiments, where the dye, or the second dye, is stoichiometric for a cell constituent, the presence of the dye, or of the second dye, on cells embedded in the tissue section is detected. In yet other preferred embodiments, a multiple measurement fluorescence scanner is used to detect the emission of light indicating close proximity of a cell to the substrate and separately, to detect the presence of the dye, or of the second dye, on a cell that is embedded in the tissue section.

The invention also features a method of characterizing a population of cancer cells in a tissue section, the method being able to exclude sectioned cells from inclusion in the characterized population, including: determining, preferably with a multiple measurement fluorescent scanner, the DNA content of individual cells in the tissue section; and identifying, preferably with a multiple measurement fluorescent scanner, sectioned cells by one of the methods of identifying sectioned cells provided for by the invention.

The invention also features a prepared sample including a tissue section stained with a first dye, preferably a fluorescent dye, e.g., Hoechst 33258, Hoechst 33342, or DAPI, and preferably, stoichiometric for a cellular component, e.g., a nuclear component e.g., DNA, and a substrate containing or coated with a second dye, preferably a fluorescent dye, e.g., ethidium bromide or propidium iodide, the first and the second dye being an energy transferring dye pair. In preferred embodiments, the emission spectrum of the first dye overlaps the absorption spectrum of the second dye, the overlap being sufficient to allow transfer of sufficient energy from the first dye to the second dye to allow detection of cut cells, the peak of the absorption spectrum of the first dye being sufficiently separated from the peak of the absorption spectrum of the second dye to allow a signal representing emissions from the second dye, the emissions from the second dye excited by absorbing emissions of the first dye (the emission of the first dye excited by energy of a wavelength absorbed by the first dye), to be distinguished from a signal representing emissions of the second dye excited directly by energy of the wavelength used to excite the first dye, and the peak of the emission spectrum of the first dye being sufficiently separated from the peak of emission of the second dye to allow a signal representing emissions from the second dye to be distinguished from a signal representing emissions from the first dye. In other preferred embodiments the tissue section is stained with a third dye, the third dye being stoichiometric for a cell component, e.g., a nuclear component, e.g., DNA. The third dye is chosen such that it does not interfere with the detection of the emission of the second dye, e.g., when the tissue section is irradiated with energy of the wavelength used to excite the first dye a signal representing emissions of the second dye can be distinguished from a signal representing emissions from the third dye. In yet other preferred embodiments of the prepared sample the tissue section contains a cancer cell, more preferably a cancer cell containing an abnormal amount of DNA.

The invention also features a prepared sample including: a tissue section stained with a dye, preferably a fluorescent dye, e.g., propidium iodide, and preferably stoichiometric for a cellular component, e.g., a nuclear component, e.g., DNA; a substrate capable of conducting evanescent light to the tissue section, a cut face of the tissue section being in contact with the substrate; and a means for conducting light through the substrate parallel to the cut face of the tissue section in contact with the substrate. In preferred embodiments of the prepared sample the tissue section is stained with a second dye, the second dye being stoichiometric for a cell component, e.g., a nuclear component, e.g., DNA. The second dye is chosen such that it does not interfere with detection of the first dye, e.g., when the tissue section is irradiated with light of the wavelength used to excite the first dye a signal representing emissions of the first dye can be distinguished from a signal representing emissions of the second dye. In other preferred embodiments of the prepared sample, the tissue section contains a cancer cell, preferably a cancer cell containing an abnormal amount of DNA.

An energy transfer detection system, as used herein, is a system including two energy receiving/transmitting elements. The first energy receiving and transmitting element can absorb energy, e.g., incident irradiation, and as a result of this absorption emit energy. The second energy receiving and transmitting element can absorb the energy emitted by the first element and as a result of that absorption emit a detectable signature signal different in wavelength from the energy that is absorbed or transmitted by the first element. An energy transferring dye pair is an energy transfer detection system wherein the two energy receiving/transmitting elements are dyes, e.g., fluorescent dyes.

A multiple measurement fluorescence scanner, as used herein, is an instrument capable of irradiating each one of the cells on a substrate or in a sample with one or more energy sources, simultaneously measuring the magnitudes of one or more of either fluorescent emissions at different wavelengths or scattering emissions at different angles, converting these measurements to electronic signals, and processing these signals to segment cells and to provide information to the user describing constituents of cells or various characteristics of the population of cells on the substrate. An example of such an instrument is described in U.S. Pat. No. 5,072,382, hereby incorporated by reference.

An energy emitting dye, as used herein, is a dye which upon absorbing energy, emits energy, e.g., a fluorescent dye which absorbs incident light and fluoresces.

Evanescent light, as used herein, is light energy in a light transmitting medium such as water, which is in contact with a light transmitting medium of higher refractive index, e.g., glass. The intensity of the light energy diminishes as an exponential function of the distance from the surface of the higher index medium. The constants of the exponential function are such that the energy decreases substantially in a distance equal to the wavelength of the light, i.e., in about 0.5 microns.

An optically detectable event, as used herein, is an event that includes the emission of a photon.

The invention provides for the identification of cells in contact with, or in close proximity to, the surface of the tissue section, i.e., cells in or near the plane of sectioning, and for the elimination of these cells from analysis. Identification of the cells in, or in close proximity to the plane of sectioning, identifies cells cut or otherwise damaged by sectioning. Cut or damaged cells confound analysis of tissue sections. For example, in tissue sections stained with stains specific to DNA, cells whose nuclei are cut produce a reduced signal (as compared to a cell whose nuclei have not been cut) which, by itself or in conjunction with the signal from a nearby cell can result in an artifactual and undesirable confounding signal. By providing for the identification of these cells the invention allows the use of tissue sections or slices in tissue analysis.

A tissue section or slice is the preferred sample for many types of biological sample analysis. Tissue sections are superior to samples consisting of dispersed cells because tissue sections retain many aspects of the morphology seen in situ. Furthermore the use of tissue sections eliminate the need for traumatic mechanical or enzymatic dispersion procedures which may damage the cells to be analyzed and which result in cell debris, both of cells which complicate analysis.

The invention exploits the fact that cells or nuclei in a tissue section that are cut or damaged by slicing are exposed on both cut surfaces of the section, independent of the section's thickness, and that in preparation for microscopic analysis, the section is sandwiched between transparent substrates, usually a microscope slide and cover slip. Thus the cut or damaged cells that need to be identified are brought into contact with, or at least into close proximity to, the substrates between which the sample is placed. Methods of the invention take advantage of an optical event involving a dye bound to the cells of the tissue section, the occurrence of the optical event being dependent on the close proximity of the stained cell to the substrate, to identify cut cells. The dependency of this optical event on the close proximity of the cut cell to the substrate can be generated in a number of ways, as is discussed below. Occurrence of the optical event serves as a signal to mark a cell as being in contact with, or in close proximity to the substrate. Exclusion of these marked cells from analysis excludes cells in or near the plane of section and thus excludes cells cut or damaged by sectioning.

Sectioned cells, or at a finer level of resolution, cells containing sectioned organelles or sectioned subcellular compartments, e.g., a sectioned nucleus or a sectioned vacuole, can be identified. If the dye bound to the cells is distributed throughout the cytoplasm the technique marks sectioned cells. If the dye stains a particular organelle or subcellular compartment, e.g., the nucleus, or a vacuole, the technique marks cells wherein that organelle or subcompartment is sectioned.

The methods of the invention can be implemented on instruments that scan the sample and collect data manually, automatically, or by a combination of manual and automatic manipulations.

Cancer cell discrimination, cell segmentation and accurate DNA constituent measurement are best done by a multiple measurement fluorescence scanning instrument on the preferred sample, tissue sections. However, even with this technique, it has not been possible to distinguish whole cells from cells whose nuclei have been cut through by the tissue sectioning knife. Such cut cell nuclei will, when measured, give an aberrant DNA value. Embodiments that combine methods disclosed herein with the multiple measurement fluorescence scanning instrument disclosed in U.S. Pat. No. 5,072,382, allow this instrument to be used with tissue sections.

This instrument measures all of the properties measurable by flow cytometers plus other morphological properties of cells placed on a solid substrate such as a slide. Briefly, this instrument uses a computer controlled stage and a resonant galvanometer scanner to position the image of a laser beam on to a cellular specimen on a slide. Multiple fluorescence and scatter emissions from illuminated cells are simultaneously detected, and using a computer, the data for each cell is properly assembled and calibrated to provide accurate constituent values such as the DNA for each cell on the slide. More than one constituent may be measured simultaneously. For example, cells stained to produce fluorescence proportional to their DNA cannot only provide per cell DNA values, they can be located based on their DNA fluorescence, and other fluorescence wavelengths resulting from other fluorochromes such as fluorescent dye tagged antibodies or RNA stains can be measured and summed in the neighborhood of the DNA fluorescence. These measurements are done automatically at cell rates of hundreds per second which rate is adequate for research and clinical use. The user can interact with this instrument, either designating cells or areas on the slide to be scanned, or the user can view cells with given sets of properties such as cells with aberrant DNA's to confirm their pathology.

Combining methods of the invention with the features of this instrument allow the user to locate, and return to areas of the tissue section that are believed to contain cells of the type of interest, e.g., cancer cells, based on the morphology of the tissue section or on the presence of cells exhibiting some other characteristic e.g., altered DNA levels. Thus data can be gathered on a subset of cells in a particular region of the sample believed to be enriched for cells of the type in interest, e.g., in the case of cancer cells, cells that depart from the normally observed levels of DNA. Furthermore, cut or damaged cells, identified as such by their contact with or close proximity to the substrate, may be automatically identified or excluded from analysis by the combination of methods presented herein with the automatic data processing features of the instrument.

The methods of the invention are not limited to those in which DNA is the constituent of interest or to those that are directed to cancer diagnosis or prognosis. Dyes or stains that bind to cell constituents other than DNA can be used in the methods and prepared samples of the invention both for identifying cut or sectioned cells and for determining the presence of a cell constituent of interest. The methods of the invention can thus be applied to tissue section analysis regardless of the cell constituent or cell type of interest and regardless of the application. For example, the use of antibodies, particularly monoclonal antibodies, directed against cell constituents and coupled to the labels or dyes described above allow the marking of cells based on their possession of any site to which an antibody can be directed. These antibody conjugates can be used to mark cut cells, or if stoichiometric for the cell constituent of interest, to quantitate that constituent, or to both mark cut cells and quantitate the constituent of interest. Fluorochrome conjugated antibodies, e.g., directed against disease specific cell components or against disease specific cells, e.g., infiltrating T cells, viral components, bacterial cells or other disease specific antigens, allow the methods of the invention to be applied to tissue sections in the analysis of presence or progress of a variety of diseases, infections, or other pathological states. Any label, stain, or dye, which can mark cells and which can be selectively detected on the basis of its proximity to the surface of a tissue section, can be used in methods and combinations of the invention to identify sectioned cells.

Other features and advantages of the invention will be apparent from the following description of the preferred embodiments, and from the claims.

DESCRIPTION OF THE PREFERRED EMBODIMENTS

The drawings are first described.

DRAWINGS

MARKING SECTIONED CELLS WITH AN ENERGY TRANSFER DETECTION SYSTEM

Figure 1:
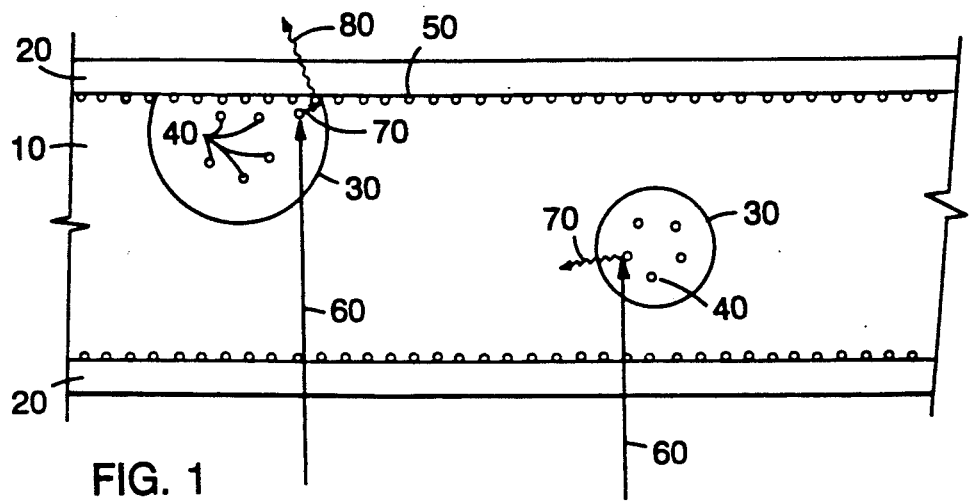
FIG. 1 is a not-to-scale diagram of a method for the identification of sectioned cells in a tissue section by energy transfer between two dyes.

Sectioned cells can be identified by virtue of their close proximity to the surface of the tissue section. In one set of techniques, as shown schematically in FIG. 1, a tissue section 10 is mounted on a substrate 20, the cells 30 in tissue section 10 are stained with dye A 40 and the stained tissue section 10 covered with another substrate 20 to yield stained tissue section 10 sandwiched between two substrates 20. Substrates 20 contain or are coated with dye B 50. Upon irradiation of the tissue section with light 60 of a wavelength absorbed by dye A 40, the dye molecules emit energy 70. Cells in contact with a substrate 20 are close enough to molecules of dye B 50 that the energy 70 emitted by dye A molecules 40 bound to those cells is absorbed by dye B molecules 50 causing the dye B molecules to emit a signature signal 80 at the position of the cell that marks the cell as a cut cell. Signature emission 80 is of a different wavelength than that of the incident irradiation 60 or the energy emitted by dye A 40. Emissions 70 of dye A molecules 40 on cells 30 that are not in contact with the substrate 20 are too distant from dye B 50 molecules for the emission 70 of dye A molecules 40 to excite dye B molecules 50 into an emission. The transfer of energy from the dye binding the cut cell to the dye in or on the substrate cannot take place where the distance between the dye with which the cells are stained and the substrate is greater than about 100 Angstroms. The theory and application of dye pairs as just described are reviewed in L. Stryer, Fluorescence Energy Transfer as a Spectroscopic Ruler, Ann. Rev. Biochem. 47, pp 819-846, 1978, the disclosure of which is hereby incorporated by reference.

Figure 2:
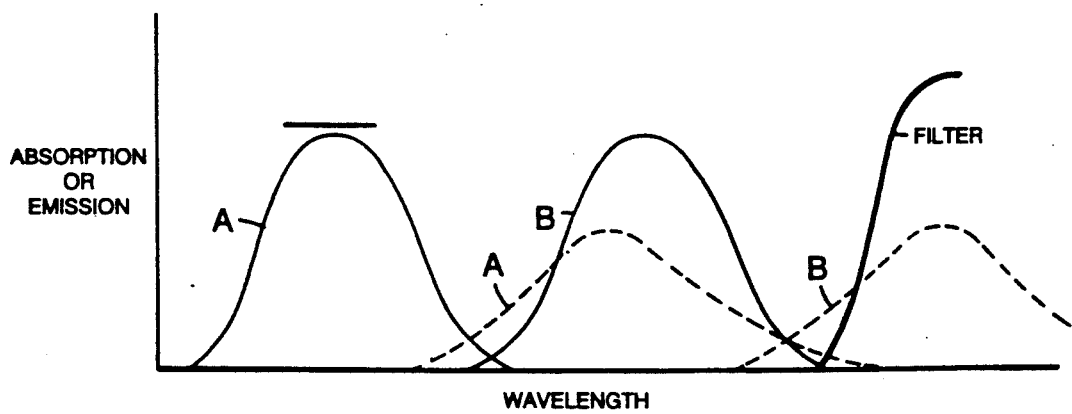
FIG. 2 is a not-to-scale representation of the absorption and emission spectra of two dyes.

In this method the emission spectrum of dye A 40 (within which is energy 70) must overlap the absorption spectrum of dye B 50 and incident irradiation 60 must be substantially incapable of exciting dye B 50 to emit signature signal 80. The overlap between the emission spectrum of dye A 40 and the absorption spectrum of dye B 50 must be sufficient to allow transfer of sufficient energy from the dye A 40 to dye B 50 to allow detection of cut cells. The peak of the absorption spectrum of dye A must be sufficiently separated from the peak of the absorption spectrum of dye B 50 to allow a signal representing emissions from dye B 50, the emissions from dye B 50 excited by absorption of emissions of dye A 40 (the emission of dye A 40 excited by energy of a wavelength absorbed by dye A 40), to be distinguished from a signal representing emissions of dye B 50 excited directly by energy of the wavelength used to excite dye A 40. The peak of the emission spectrum of dye A 40 must be sufficiently separated from the peak of emission of dye B 50 to allow a signal representing emissions from dye B 50 to be distinguished from a signal representing emissions from dye A 40. The relationship between the absorption and emission spectra of dyes A and B are shown in FIG. 2. In FIG. 2 absorption spectra are indicated by solid lines, emission spectra are indicated by broken lines, and the behavior of a filter that allows detection of substantially only the emission of dye B is shown by a bold line. The bar over the absorption spectrum of dye A indicates the preferred range of the incident irradiation 60 used to excite dye A. Dyes A and B, and the wavelength of incident irradiation 60, are chosen such that the emission of dye B can be measured, e.g., with a filter possessing the transmission characteristics shown in FIG. 2. The filter passes wavelengths longer than its cutoff, and thus allows sampling of energy that is derived substantially only from the emission of dye B. Since the function defining the emission spectra of dyes A and B are continuous functions, emission of dye A molecules make some contributions (noise) to the measurement of the emission of dye B (signal). The dyes are chosen such that the noise contribution of dye A emissions to the sample are not so great as to obscure the signal from dye B, i.e., the signals can be distinguished.

If dye A is not stoichiometric for the constituent of interest, measurement of that constituent is made with a third dye. The third dye, dye C, is chosen such that it does not interfere with the detection of the emission of dye B, e.g., when the dye C is irradiated with energy of the wavelength used to excite the dye A a signal representing emissions of the dye B can be distinguished from a signal representing emissions from the dye C.

MARKING SECTIONED CELLS WITH SUBSTRATE TRANSMITTED ENERGY

Figure 3:
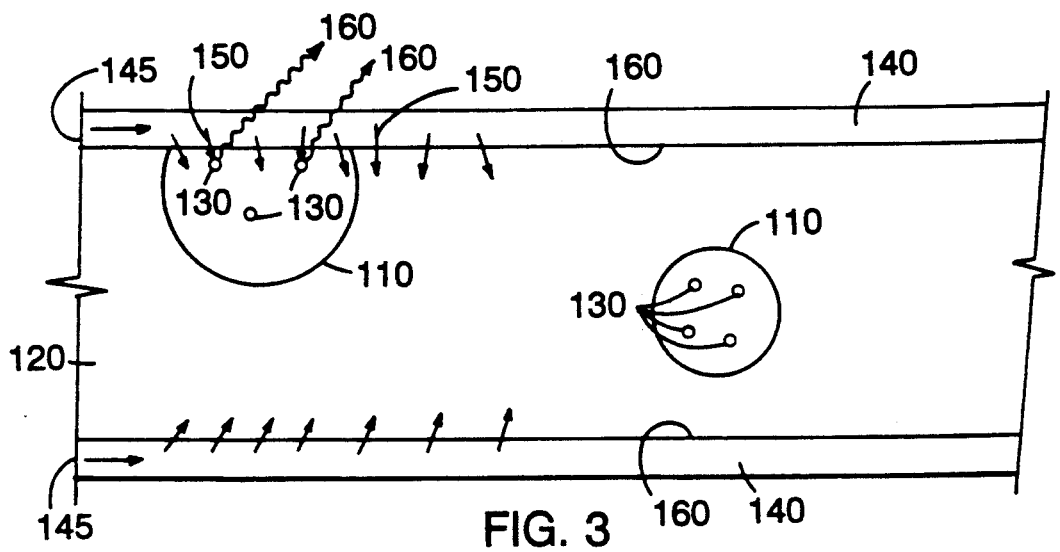
FIG. 3 is a not-to-scale diagram of a method for the identification of sectioned cells in a tissue section by irradiation with evanescent light.

Evanescent light passing the interface between a tissue section and a substrate with which the tissue section is in contact with can be used to induce an optical event that marks cells at the surface of the tissue section. The substrate itself used as a light pipe and thus is caused to transfer energy, by evanescence, to regions in close proximity to its surfaces. As shown schematically in FIG. 3, the cells 110 of a tissue section 120 are stained with a dye 130, e.g., propidium iodide if the constituent of interest is DNA, and the tissue section 120 placed between substrates 140. Light enters substrate 140 at substrate edge 145. If the refractive index of tissue section 120 is less than the refractive index of substrate 140 some of the incident light entering at substrate edge 145 will be trapped with substrate 140 acting as a light pipe, and some will enter tissue section 120 as an evanescent waves 150. Waves of evanescent light 150 of a wavelength that is absorbed by dye molecules 130 pass the interface 160 between the substrate 140 and the tissue section 120. Dye molecules 130 bound to cells in contact with the substrate are within the range of penetration of the evanescent waves 150 and absorb evanescent light to be excited to produce signature signal 160. Dye molecules 130 on cells 110 that are not within the range of the evanescent waves 150 are not excited and do not produce a signature signal. As mentioned above the intensity of the evanescent waves that enter the tissue section decrease very rapidly with distance from the substrate/tissue section interface and are very substantially reduced within a distance equal to the wavelength of light. Thus the intensity of evanescent light is reduced to insignificant levels well within a distance equivalent to the diameter of a typical cell.

If dye 130 is stoichiometric for the cell constituent of interest, it is used to quantitate the constituent of interest. If the dye 130 is not stoichiometric for the cell constituent of interest, a second dye, stoichiometric for the constituent of interest is used to quantitate the constituent of interest. The second dye is chosen such that it does not interfere with the measurement of dye molecules 130, e.g., when the second dye is irradiated with light at the wavelength of the evanescent light 150 used to excite dye 130, a signal representing emissions of dye 130 can be distinguished from a signal representing emissions of the second dye.

THE IDENTIFICATION OF CELLS CONTAINING SECTIONED NUCLEI IN TISSUE SECTIONS BY ENERGY TRANSFER BETWEEN TWO DYES

Two dyes, dye A and dye B, forming an energy transferring pair, such that dye A is used to stain nuclei and dye B is excited into fluorescence by dye A, can be incorporated into a method of identifying cells containing sectioned nuclei in tissue slices. If the absorption spectrum of dye B overlaps the emission spectrum of dye A, such dye pairs can transfer energy effectively over distances of the order of 100 Angstroms or less. To identify cut nuclei, dye A may or may not be stoichiometric for a constituent such as DNA but it must stain the cell nucleus with little cytoplasmic staining. It should fluoresce when illuminated by a light source such as the image of a laser or arc lamp. The slide and cover slip, or thin transparent gels between the section and the slide and between the section and the cover slip, are coated with or contain dye B, which can accept energy from the emitting dye A and remit energy at a longer wavelength, producing a unique fluorescent color emission. When irradiated with light of the appropriate wavelength, dye A, bound to the nuclei of the section, fluoresces. If the nuclei-bound dye is within close proximity to the dye B-coated substrates (within about 100 Angstroms or less) then energy is transferred to dye B molecules and those excited dye B molecules fluoresce. The emission of dye B is detected, along with a different color emission (from another dye, preferably dye A, that is stoichiometric for the constituent of interest) proportional to the constituent of interest, such as DNA. Whenever dye B emission is greater than a user determined threshold value that cell's data are excluded from inclusion in the constituent distribution.

This method is implemented as follows. An ordinary microscope slide is coated with a gel containing fluorescent dye B. A histology section from the specimen to be assayed is placed on the slide and stained by dipping the slide into dyes and fixatives as is presently done in pathology laboratories. Fluorescent dye A is used to stain the cell nuclei. If dye A is stoichiometric for the constituent of interest no other dye need be added. If it is not, a third dye, stoichiometric for the constituent of interest, is also used to stain the section. The section is then covered with a cover slip coated with the same dye B containing gel as the slide and the coverslip sealed at the edges. The histology section whose nuclei are stained with dye A (and, if dye A is not suitable for quantitation of the constituent of interest, then also a third dye which is stoichiometric for the constituent of interest) is thus sandwiched between two dye B containing surfaces.

Dye A can be a nuclear dye taken from the group of dyes Hoechst 33258, Hoechst 33342, or DAPI. Dye A is used as a tissue stain at concentrations near 5 $\mu$M. At this concentration these dyes are stoichiometric for DNA and show only nuclear fluorescence when examined microscopically. They absorb light at wavelengths near 3500 Angstroms and fluoresce at wavelengths near 5000 Angstroms. Light sources using either a Helium Cadmium laser or a Mercury arc lamp are appropriate for exciting these dyes' fluorescence. The dyes ethidium bromide or propidium iodide are suitable energy acceptors (dye B) having high extinction near the emission peak of the above dyes (dye A's) and emitting light at wavelengths above 6000 Angstroms, well separated from the emissions of the above dyes (dye A's). Since these dyes (dye B) need not be stoichiometric their concentration, which should be above 50 ug/ml in the gel coating on the slide and cover slip contacting the histology section, should not be critical.

The sample is irradiated with light near 3500 Angstroms in wavelength. Cells showing emission at wavelengths above 6000 Angstroms are in close proximity (within about 100 Angstroms) with one of the substrates and are thus marked as cells with a high probability of being sectioned.

THE AUTOMATED ANALYSIS OF CELLS CONTAINING SECTIONED NUCLEI IDENTIFIED BY ENERGY TRANSFER BETWEEN TWO DYES

The tissue section, stained with dye A and placed between substrates coated with or containing dye B, as described above, is placed on the stage of the multiple measurement fluorescent scanner described in U.S. Pat. No. 5,072,382. A Helium Cadmium laser is used as a light source. Fluorescent emission from the slide is measured by two photodetectors, the first measuring in a range near 5000 Angstroms, and the second in a range near 6000 Angstroms.

As each cell is scanned by the laser beam it will emit fluorescence. In this embodiment, each cell will emit light at 5000 Angstroms. This light is detected by a photomultiplier, sampled and converted by an A/D converter into a sequence of digital values stored in computer memory as described in detail below and in the copending application. Cells are detected by virtue of the presence of a measurement that exceeds a user determined threshold, i.e., by a peak of fluorescence. A window is centered on the peak value, and values for each pixel in the window (minus a background value determined from measurements taken in an adjacent window) are recorded. The values are modified by a calibration value matrix to yield a number representative of that cell's DNA.

Figure 4:
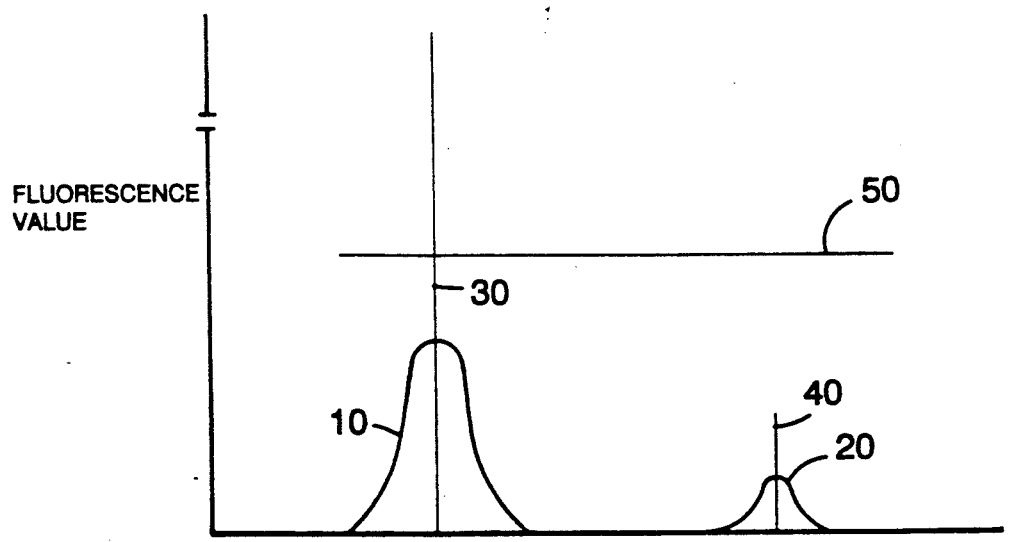
FIG. 4 is a not-to-scale representation of the fluorescence values of cut and uncut cells.

The fluorescence at 6000 Angstroms is also independently detected by a second photomultiplier and processed exactly as the DNA value—the same neighborhood centered on the peak value of the DNA dye emission from the cell is used to position the additional matrix for this second set of values. The resulting second total can be compared to a user determined threshold value. The relationship between the measured value for uncut cells, cut cells, and the user determined threshold value is shown diagrammatically in FIG. 4. In FIG. 4 curve 10 represents the fluorescence, over time, of a typical scan of a cut cell and curve 20 represents the fluorescence, over time, of a typical scan of an uncut cell. A window is centered on the peak value and values for each pixel in the window (minus a background value determined from measurements taken in an adjacent window) are recorded and summed. This results in a summed value for a typical cut cell, represented by value 30 in FIG. 4, and a summed value for a typical uncut cell, represented by value 40 in FIG. 4. Threshold value 50 represents a user determined threshold which is chosen to distinguish the two cell populations. If a summed value is above the user determined threshold value, the cell is marked in the cell data list as having a nucleus that is touching the slide or cover slip. During subsequent data analysis and display routines such marked cells can be eliminated from analysis and display, if desired. Alternatively, the second value may be stored in the data list along with the DNA value. During subsequent analysis routines, the second value may be tested against a user set threshold value to determine the appropriate level to discriminate cut from uncut nuclei.

THE IDENTIFICATION OF SECTIONED CELLS IN TISSUE SLICES BY IRRADIATION WITH SUBSTRATE-TRANSMITTED ENERGY USING AUTOMATED TISSUE ANALYSIS

A histology section is prepared, by methods known to those skilled in the art, and placed on a microscope slide. The section is stained with a dye specific to the cell constituent of interest, in the case of DNA with a DNA specific fluorescent dyes, such as propidium iodide at a concentration near 50 ug/ml. The section is covered with a cover slip or second slide and sealed at the edges. Thus, the section is sandwiched between two glass plates or substrates.

The sandwich described above is placed on the stage of an automated analytical instrument, e.g., the apparatus described in U.S. Pat. No. 5,072,382. If the apparatus described in U.S. Pat. No. 5,072,382 is used, the stage of the apparatus is modified so that a fiber optical bundle strip is placed in contact with one edge of each of the top and bottom glass plates. Such fiber optic bundles are available commercially in a shape appropriate to cause light entering the fibers on one end to be transmitted into one end of each glass plate. The fibers are illuminated with a light source of wavelength that will excite the fluorescence of the nuclear stain used in the section. For propidium iodide this could be an Argon ion or green Helium Neon laser or an arc lamp filtered to provide light near 5000 Angstroms. It is possible that the light source could be the same as the primary instrument light source.

It is necessary that the apparatus be provided with an aperture, at which plane the cell image is in focus, between the scanning mirror and the photomultiplier that will be used to measure DNA fluorescence. In all present embodiments of the apparatus described in U.S. Pat. No. 5,072,382 such an aperture is used to reduce stray light. The aperture causes the photomultiplier to see only light coming from the specific pixel being scanned by the resonant galvanometer mirror. Thus, one photomultiplier will detect the light from only that pixel even if all cells on the slide are fluorescing.

Although it is possible to electronically alternate fluorescence excitation with the fiber bundle light source and the standard source on a cell by cell or scan strip by strip basis, a simpler embodiment in which the slide is scanned twice is described below. The slide is first scanned with the fiber bundle light source turned off. If the source is a laser, the current to it is electronically reduced. If the same source is used for the primary source an electronic shutter is used. The designated area of the histology section is scanned and processed exactly as described in U.S. Pat. No. 5,072,382. After the area is scanned and the data list stored, the primary source is turned off or shuttered and the slide is rescanned with excitation only from the optical fiber bundle. This will cause both glass plates to act as light pipes since the refractive index of the histology section is lower than the glass. Some of this energy will enter the histology section as a short range evanescent wave causing only dye in contact with the glass to fluoresce. Since only cut nuclei have nuclear dye in contact with the glass surfaces only the cut cells will fluoresce. The designated area of the slide is rescanned and processed exactly as described above. The data is stored as a list in memory.

After each test, both data lists are read from memory and the measurement data for each cell are merged. The merge key is the cell location in each of the two data lists which is one of the properties always stored for every cell detected. The user can then select cells that have total fluorescence values from the primary source representing the DNA of each cell and having total fluorescence below a user selected threshold from the fiber optic source. Such selected cells will only be the intact nuclei and their DNA frequency distributions or other properties can be displayed and further processed.

Other embodiments are within the following claims.

What is claimed is:

1. A method of identifying a sectioned cell in a tissue section comprising supplying a tissue section, supplying an energy transferring dye pair, said dye pair comprising a first dye and a second dye, the emission spectrum of said first dye overlapping the absorption spectrum of said second dye, said overlap being sufficient to result in a detection enabling amount of energy transfer from said first dye to said second dye, the peak of the absorption spectrum of said first dye being sufficiently separated from the peak of the absorption spectrum of said second dye to allow a signal representing emissions from said second dye, said emissions from said second dye excited by absorbing emissions from said first dye, said emissions from said first dye excited by energy of a wavelength absorbed by said first dye, to be distinguished from a signal representing emissions of said second dye excited directly by energy of said wavelength used to excite said first dye, and the peak of the emission spectrum of said first dye being sufficiently separated from the peak of emissions of the second dye to allow a signal representing emissions from the second dye to be distinguished from a signal representing emissions from the first dye, staining the cells of said tissue section with said first dye, contacting a cut surface of said stained tissue section with said second dye, irradiating said stained tissue section with energy in the absorption spectrum of said first dye, and detecting a signal representing the emissions of said second dye, said signal indicating the presence of a sectioned cell.

2. A method of characterizing a population of cancer cells in a tissue section, said method being able to exclude sectioned cells from inclusion in the characterized population, comprising determining the DNA content of individual cells in the tissue section, identifying cancer cells which exhibit aberrant DNA content in said tissue section, identifying sectioned cells by the method of claim 1, allowing the exclusion of said sectioned cells from inclusion in said characterized population of cancer cells.

3. A method of identifying a sectioned cell in a tissue section comprising supplying a tissue section, supplying an energy emitting dye, staining the cells of said tissue section with said dye, contacting said stained tissue section with a substrate, passing light through said substrate parallel to the plane of the tissue section and measuring the emission of light of the wavelength emitted by said dye when said dye is excited by evanescent light passing through the interface between the substrate and the tissue section, the emission of said light indicating close proximity of said cell to said substrate.

4. A method of characterizing a population of cancer cells in a tissue section, said method being able to exclude sectioned cells from inclusion in the characterized population, comprising determining the DNA content of individual cells in the tissue section, identifying cancer cells which exhibit aberrant DNA content in said tissue section, identifying sectioned cells by the method of claim 3, allowing the exclusion of said sectioned cells from inclusion in said characterized population of cancer cells.

* * * * *